(12) United States Patent
Ray

(10) Patent No.: US 8,449,555 B1
(45) Date of Patent: May 28, 2013

(54) PEDICLE PROBE

(76) Inventor: Terry L. Ray, Gilbert, AZ (US)

( * ) Notice: Subject to any disclaimer, the term of this patent is extended or adjusted under 35 U.S.C. 154(b) by 1699 days.

(21) Appl. No.: 10/400,711

(22) Filed: Mar. 27, 2003

Related U.S. Application Data

(60) Provisional application No. 60/368,273, filed on Mar. 27, 2002.

(51) Int. Cl.
*A61B 17/56* (2006.01)
(52) U.S. Cl.
USPC .......................................................... 606/102
(58) Field of Classification Search
USPC ............... 606/102, 67, 72, 73, 79, 80, 81, 86, 606/91, 95, 96, 99, 100, 104, 106; 433/72; 408/224, 225; 600/38–41
See application file for complete search history.

(56) References Cited

U.S. PATENT DOCUMENTS

| | | | | |
|---|---|---|---|---|
| 1,726,193 A * | 8/1929 | Ross | ................................ | 33/514 |
| 2,226,949 A * | 12/1940 | Simpson | ..................... | 84/477 B |
| 2,692,001 A * | 10/1954 | Hawkinson | .................... | 152/370 |
| 2,923,063 A * | 2/1960 | Hansen | ............................ | 33/560 |
| 4,041,558 A * | 8/1977 | Victor | ................................ | 7/158 |
| 4,314,575 A * | 2/1982 | Kuo | .................................. | 135/66 |
| 4,373,285 A * | 2/1983 | Grout et al. | ......................... | 42/90 |
| 4,890,406 A * | 1/1990 | French | ............................... | 42/90 |
| 5,129,904 A * | 7/1992 | Illi | .................................... | 606/72 |
| 5,242,448 A | 9/1993 | Pettine et al. | | |
| 5,365,631 A * | 11/1994 | Emerick | ........................... | 15/105 |
| 5,382,251 A * | 1/1995 | Hood et al. | ...................... | 606/99 |
| 5,492,452 A * | 2/1996 | Kirsch et al. | ..................... | 411/455 |
| 5,519,973 A * | 5/1996 | Keith et al. | ....................... | 52/410 |
| 5,573,537 A | 11/1996 | Rogozinski | | |
| 5,665,121 A * | 9/1997 | Gie et al. | ........................ | 128/898 |
| 5,910,172 A * | 6/1999 | Penenberg | .................. | 623/23.21 |
| 5,928,243 A | 7/1999 | Guyer | | |
| 5,971,985 A * | 10/1999 | Carchidi et al. | ................. | 606/61 |
| 6,022,354 A * | 2/2000 | Mercuri et al. | .................. | 606/80 |
| 6,146,385 A * | 11/2000 | Torrie et al. | ...................... | 606/96 |
| 6,200,323 B1 * | 3/2001 | Pierson, III | ..................... | 606/102 |
| 6,241,734 B1 * | 6/2001 | Scribner et al. | .................. | 606/93 |
| 6,318,515 B1 * | 11/2001 | Pirrallo | ............................ | 188/78 |
| 6,398,785 B2 * | 6/2002 | Carchidi et al. | ................. | 606/73 |

* cited by examiner

*Primary Examiner* — Eduardo C Robert
*Assistant Examiner* — David Comstock
(74) *Attorney, Agent, or Firm* — Parsons & Goltry; Robert A. Parsons; Michael W. Goltry

(57) ABSTRACT

A bone probe and method of use, for probing a hole formed in a bone. The bone probe includes a head having a peripheral edge, a tail member, and a shaft coupled therebetween. The peripheral edge of the head engages the sides defining a hole in the bone and transmits vibrations along the shaft to the tail member.

2 Claims, 3 Drawing Sheets

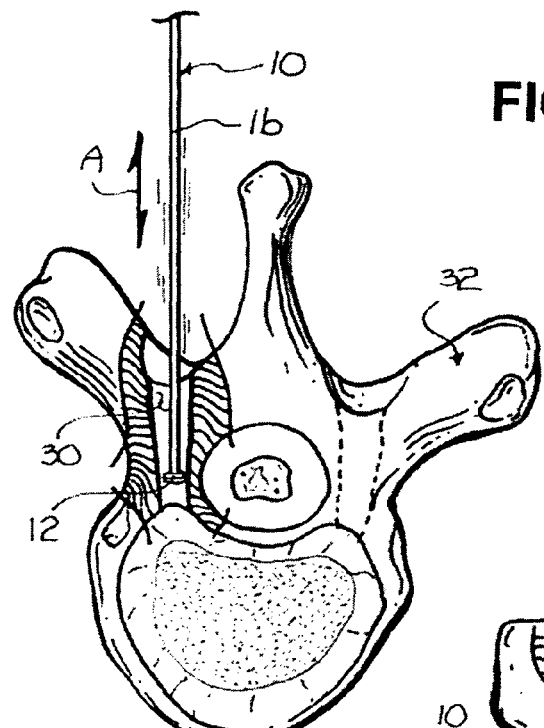
FIGURE 5
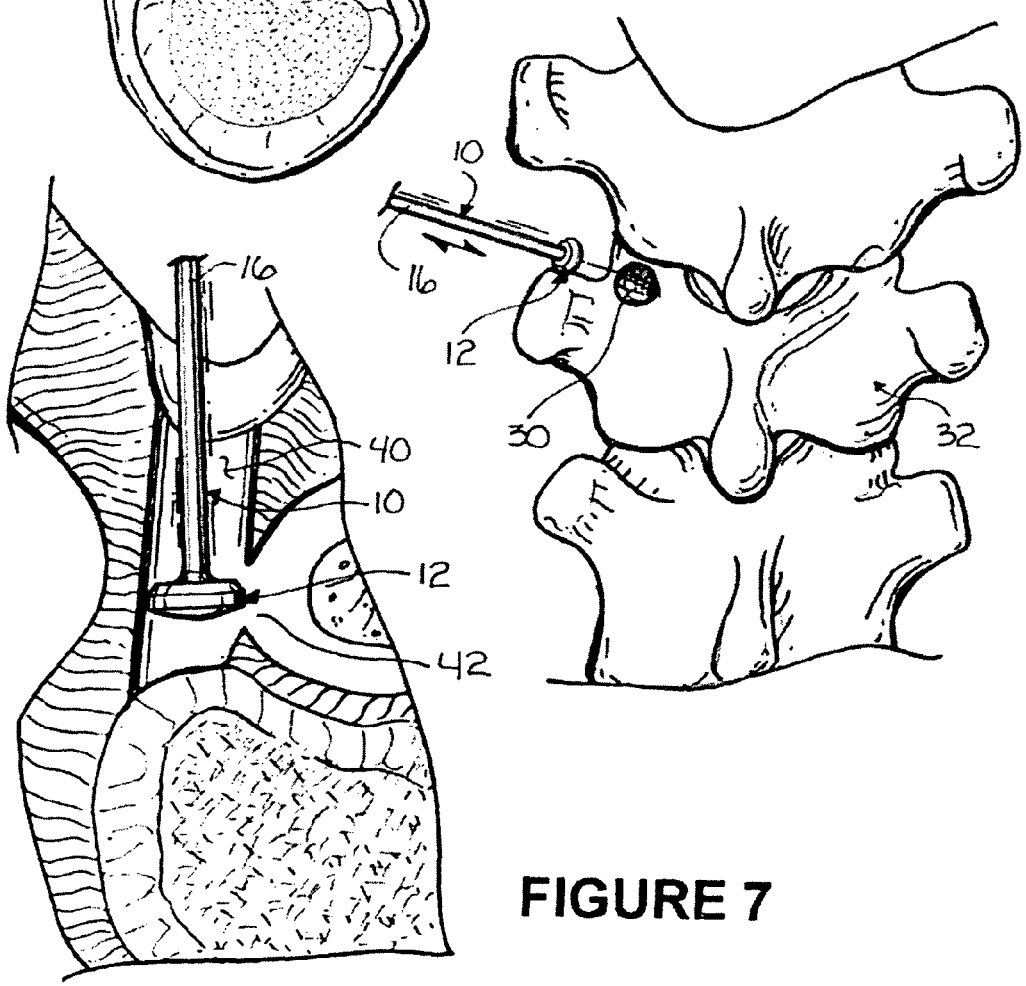
FIGURE 6
FIGURE 7

PEDICLE PROBE

CROSS-REFERENCE TO RELATED APPLICATION

This application claims the benefit of U.S. Provisional Patent Application No. 60/368,273, filed 27 Mar. 2002.

FIELD OF THE INVENTION

This invention relates to medical instruments.

More particularly, the present invention relates to bone probes.

BACKGROUND OF THE INVENTION

During some orthopedic procedures, holes are drilled into bone for fasteners such as screws. This is particularly common in procedures involving the vertebrae of the spinal column. Spinal fixation, such as sacral fusion, requires holes in the bone of the vertebrae to accommodate implant fixation components. These holes, for example, are often formed in the pedicle. Misaligned or improperly positioned holes can result in weakening of the bone or even breaches in the bone. Weakening of the bone or breaches therein can cause serious complications, particularly when the spinal column is involved.

Bone probes are often employed to determine if a hole is properly positioned, determining the angle and the like. A common bone probe includes a hooked end. A primary problem with this implement is that the hooked end is often too big to be inserted into a drill hole. When the hook is reduced to allow insertion through the hole, it is often too small to be effective. The problems have been overcome to some extent by a probe of super elastic material carried within a cannula. The cannula sheaths the probe in a substantially straight configuration and can be easily inserted into the hole. The probe is then extended from the cannula at which time it returns to a hooked configuration. While somewhat effective, this device can be difficult to employ and may be costly. Additionally, the sensitivity of the probe is reduced by its flexibility and its position within the cannula.

It would be highly advantageous, therefore, to remedy the foregoing and other deficiencies inherent in the prior art.

Accordingly, it is an object of the present invention to provide a new and improved bone probe.

Another object of the invention is to provide a bone probe which is easily used.

And another object of the invention is to provide a bone probe which can be used without a specific orientation.

SUMMARY OF THE INVENTION

Briefly, to achieve the desired objects of the instant invention in accordance with a preferred embodiment thereof, provided is a bone probe and method of use, for probing a hole formed in a bone. The bone probe includes a head having a peripheral edge, a tail member, and a shaft coupled therebetween. The head includes a rearward surface from which the shaft centrally extends and a forward surface opposite the rearward surface.

In a specific aspect, the rearward surface is generally circular and the forward surface is generally circular. In either aspect, the edge is defined at the junction of a forward peripheral surface extending from the forward surface and a rearward peripheral surface extending from the rearward surface.

In yet another aspect of the invention, the edge is defined at the junction of a peripheral surface extending from the rearward surface, and the forward surface.

Also provided is a method of probing a hole in a bone. The method includes providing a bone having a hole therein and providing a bone probe including a head having a peripheral edge and a shaft extending therefrom. The head is inserted into the hole in the bone and moved in a reciprocating manner within the hole with the shaft. The peripheral edge of the head engages walls defining the hole in the bone and generates vibrations from engagement between the peripheral edge and the walls of the hole. The vibrations are transmitted along the shaft.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which:

FIG. 5 is a perspective view illustrating the bone probe of FIGS. 1-4 being inserted into a drill hole in a vertebra;

FIG. 6 is a top plan view illustrating the bone probe in a properly drilled hole;

FIG. 7 is an enlarged top plan view illustrating the bone probe in a drilled hole having a breach;

DETAILED DESCRIPTION OF THE PREFERRED EMBODIMENT

Figure 1:
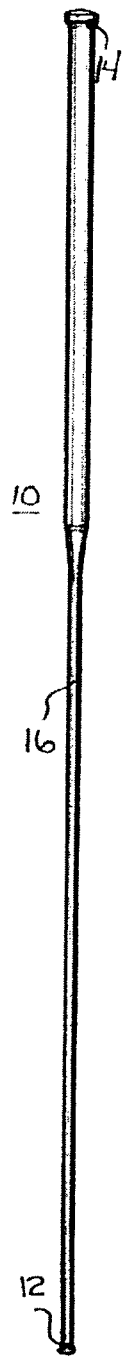
FIG. 1 is a plan view of a bone probe according to the present invention.

Turning now to the drawings in which like reference characters indicate corresponding elements throughout the several views, attention is first directed to FIG. 1 which illustrates a bone probe generally designated 10. Bone probe 10 includes a head 12, a tail member 14 and a shaft 16 coupled therebetween. Head 12, tail 14 and shaft 16 are formed as a unitary body from a rigid material. The unitary nature of probe 10 permits transmission of vibrations from head 12 to tail 14. The vibrations are generated due to the shape of head 12, which will be described presently. Tail 14 is designed to mimic head 12 by the vibrations transmitted along shaft 16. Probe 10 is preferably fabricated of metal such as stainless steel, etc., providing the required rigidity and vibration transmission characteristics.

Figure 2:
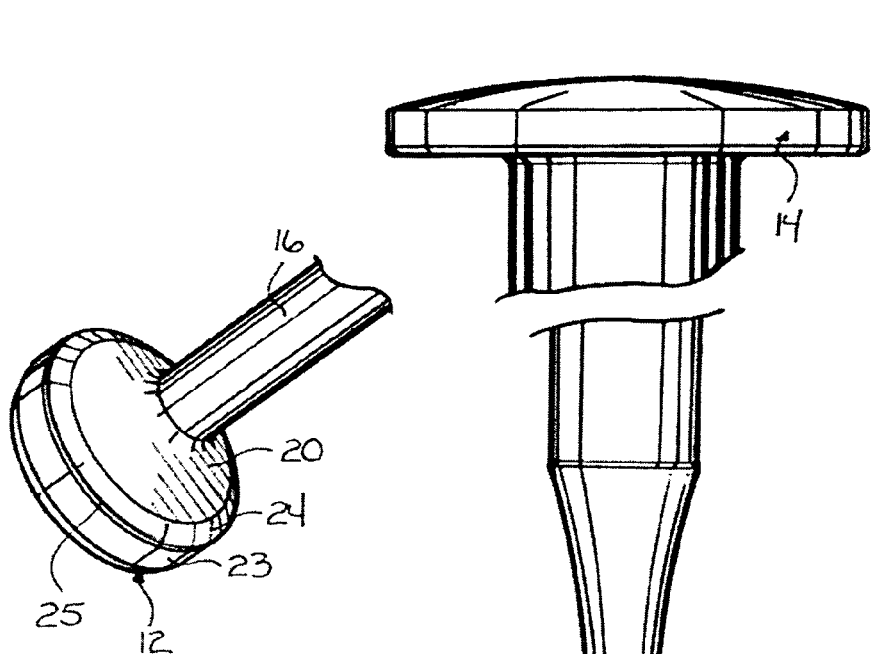
FIG. 2 is an enlarged segmented view of the bone probe of FIG. 1 with a portion in cross-section.

With additional reference to FIG. 2, head 12 is smaller than tail 14, and sized to be received within a drill hole to be probed. Shaft 16 has an initial diameter smaller than head 12 and slightly increases in diameter along a first length being approximately 60% of the total length, and increases to a handle portion terminating in tail member 14. Tail member 14 is larger than head 12, to provide sufficient tactile surface for an operator to feel the vibrations transmitted from head 12.

Figure 3:
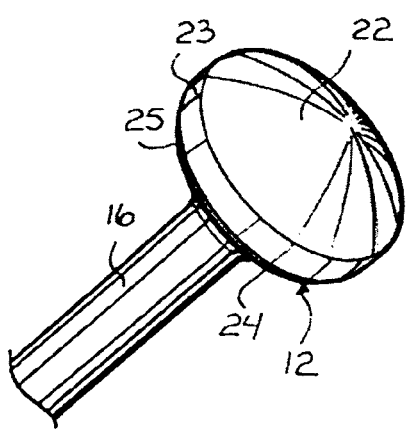
FIG. 3 is a rear perspective view illustrating the head of the bone probe of FIGS. 1 and 2.
Figure 4:
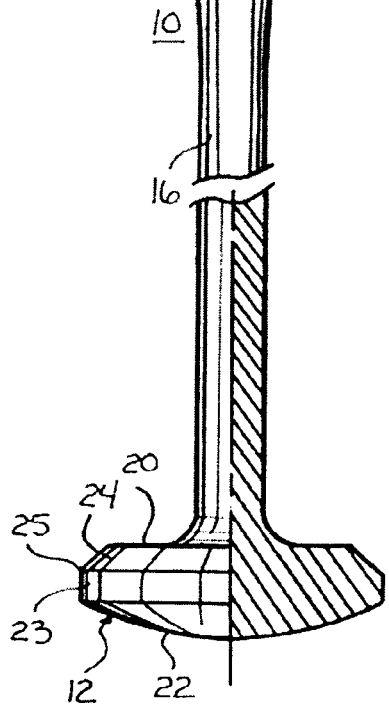
FIG. 4 is a front perspective view illustrating the head of the bone probe of FIGS. 1 and 2.

Still referring to FIG. 2, with additional reference to FIGS. 3 and 4, head 12 is generally button shaped, and includes a rearward surface 20 from which shaft 16 centrally extends, a forward surface 22 opposite rearward surface 20, a forward peripheral surface 23 and a rearward peripheral surface 24. Shaft 16 is substantially straight to facilitate insertion into a drill hole. Forward surface 20 is generally circular and has a slight domed or convex shape. Forward peripheral surface 23 extends substantially perpendicularly from the periphery of forward surface 22. Rearward peripheral surface 24 extends at an angle from forward peripheral surface 23 toward shaft 16, terminating in rearward surface 20. An edge 25 is formed at the junction of forward peripheral surface 23 and rearward peripheral surface 24. Edge 25 produces the vibration that are transmitted along shaft 16 to tail member 14, as will be described presently. Edge 25 extends around the entire periphery therefore, the rotational orientation of head 12 is unimportant to the effective use thereof. In other words, edge 25 can be brought into contact with the sides of the hole from any rotational position, and does not require a specific direction of the handle as in bone probes having hooked ends. It will be understood by those skilled in the art that an edge similar to edge 25 can be formed about a periphery of head 12 with other shapes. For example, a ridge can be formed around the periphery of a head and is considered an edge for purposes of this description.

Turning now to FIGS. 5 and 6, an example of a use of bone probe 10 is illustrated. A drill hole 30 is formed in a vertebra 32 to receive a pedicle screw (not shown) to anchor a device. Head 12 of probe 10 is inserted into drill hole 30 and moved along the sides of the hole in a reciprocating motion as indicated by double arrowed line A. In this specific example, drill hole 30 is formed in the cancellous tissue of the vertebra through the pedicle into the vertebral body. The passage thus created has a relatively rough surface. By moving head 12 along the sides of the passage in a reciprocating motion, edge 25 engages the surface of drill hole 30 and transmits the vibrations generated from contact with the rough surface along shaft 16 to tail member 14. The operator can feel these vibrations and determine that no breach in the vertebra has occurred.

Referring to FIG. 7, an improperly formed drill hole 40 has been created. In this instance, due to the angle of the hole, the thickness of the vertebra or numerous other reasons, a breach 42 has been created. This is an undesirable occurrence which needs to be known. By moving head 12 along the surface of drill hole 40, vibrations are generated by edge 25 engaging the rough surface of drill hole 40. As head 12 passes over breach 42, a dead space is detected. Edge 25 is no longer generating vibrations against a rough surface, therefore no vibrations are transmitted to tail member 14. This lack of vibration indicates a beach in the vertebra. Subsequent actions can now be taken as necessary.

Figures 8, 9:
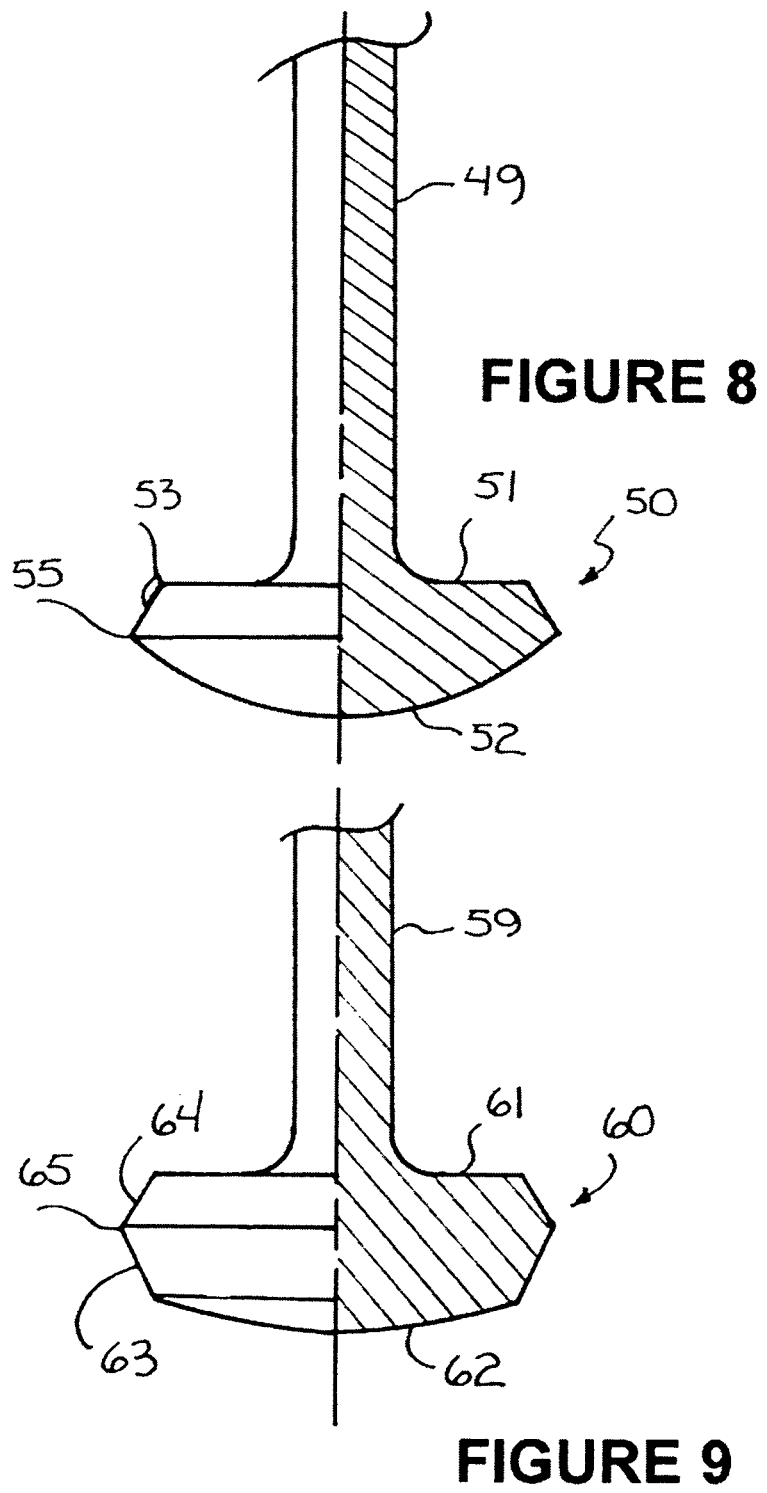
FIG. 8 is an enlarged view of another embodiment of a head of a bone probe with a portion in cross-section.
FIG. 9 is an enlarged view of yet another embodiment of a head of a bone probe with a portion in cross-section.

Turning now to FIG. 8, another embodiment of a head, generally designated 50, is illustrated. Head 50 is generally button shaped, and includes a rearward surface 51 from which a shaft 49 centrally extends, a forward surface 52 opposite rearward surface 51 and a peripheral surface 53. Head 50 differs from head 12 in that a single peripheral surface is employed. Forward surface 52 is generally circular and has a slight domed or convex shape. Peripheral surface 53 extends at an angle from the periphery of forward surface 52. An edge 55 is formed at the junction of peripheral surface 53 and forward surface 52. Edge 55 is the portion of head 50 furthest from shaft 49, so as to easily engage a surface of bone. Edge 55 produces the vibrations that are transmitted along shaft 49 to the tail member, as was described previously.

Turning now to FIG. 9, another embodiment of a head, generally designated 60, is illustrated. Head 60 is generally button shaped, and includes a rearward surface 61 from which a shaft 59 centrally extends, a forward surface 62 opposite rearward surface 61, a forward peripheral surface 63 and rearward peripheral surface 64. Head 60 differs from head 12 in that forward peripheral surface 63 is not substantially perpendicular to forward surface 62, but forms a more acute angle to further delineate an edge 65 formed at the junction of forward peripheral surface 63 and rearward peripheral surface 64.

Various changes and modifications to the embodiments herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. A bone probe for probing a hole formed in a bone, comprising:
   a head having a peripheral edge;
   a tail member;
   a shaft coupled therebetween, forming a unitary body to transmit vibrations from the head to the tail member;
   the head further including a generally circular rearward surface from which the shaft centrally extends, and a generally circular forward surface opposite the rearward surface, the forward surface being convex to form a dome;
   wherein the edge is defined at the junction of a forward peripheral surface extending from the forward surface and a rearward peripheral surface extending from the rearward surface; and
   the tail member having a diameter larger than a diameter of the shaft.

2. A bone probe for probing a hole formed in a bone, comprising:
   a shaft having a diameter;
   a head having a peripheral edge and including a generally circular rearward surface from which the shaft centrally extends and a generally circular forward surface opposite the rearward surface, the forward surface being convex to form a dome;
   wherein the edge is defined at the junction of a forward peripheral surface extending from the forward surface and a rearward peripheral surface extending from the rearward surface;
   a tail member at an end of the shaft opposite the head, the tail member having a diameter larger than the diameter of the shaft; and
   the head, shaft, and tail member being formed in a one piece, unitary body to transmit vibrations from the head to the tail member wherein vibrations of the tail member mimic vibration of the head.

\* \* \* \* \*